United States Patent [19]
Tominaga et al.

[11] Patent Number: 5,801,008
[45] Date of Patent: Sep. 1, 1998

[54] METHOD OF QUANTITATIVE DETERMINATION OF PEROXIDE, A PEROXIDATION-ACTIVE SUBSTANCE OR A PYRAZOLOPYRIDOPYRIDAZINE DERIVATIVE

[75] Inventors: Yoshinori Tominaga, Nagasaki; Norihito Aoyama, Sunto-gun; Toshiyuki Masunari, Sunto-gun; Akira Miike, Sunto-gun, all of Japan

[73] Assignee: Kyowa Medex Co., Ltd., Tokyo, Japan

[21] Appl. No.: 653,711

[22] Filed: May 23, 1996

[30] Foreign Application Priority Data

May 31, 1995 [JP] Japan ................... 7-133379

[51] Int. Cl.$^6$ .................................. C12Q 1/28
[52] U.S. Cl. ..................... 435/28; 435/4; 435/25; 548/255; 546/1
[58] Field of Search .................. 544/236; 435/6, 435/7.91, 28, 4, 25; 422/52; 546/1, 249; 548/255

[56] References Cited

U.S. PATENT DOCUMENTS

| | | | |
|---|---|---|---|
| 4,842,997 | 6/1989 | Carter et al. | 435/6 |
| 4,863,689 | 9/1989 | Leong et al. | 422/52 |
| 5,106,732 | 4/1992 | Kondo et al. | 435/28 |
| 5,306,621 | 4/1994 | Kricka | 435/7.91 |
| 5,395,752 | 3/1995 | Law et al. | 435/6 |
| 5,420,275 | 5/1995 | Masuya et al. | 544/236 |
| 5,457,200 | 10/1995 | Zimmermann et al. | 544/281 |
| 5,512,451 | 4/1996 | Kricka | 435/28 |

FOREIGN PATENT DOCUMENTS

| | | |
|---|---|---|
| 0433854 | 6/1991 | European Pat. Off. . |
| 0650044 | 4/1995 | European Pat. Off. . |
| 15219 | 2/1993 | Japan . |

OTHER PUBLICATIONS

Dickinson et al., Aminocyanopyrazoles, J. Org. Chem. 1964, 29, 1915–1919, Jul. 1964.

Tominaga et al., Polycyclic Pyridazines. II [3]. Synthesis of Pyrazolol[4',3':5,6]pyrido[2,3–d]pyridazine Derivatives from Dimethyl Pyrazolo[3,4–b]pyridazine–5,6–dicarboxylates as the Key Intermediates, J. Heterocyclic Chem. Feb. 1993, 30, 267–273.

Cheng et al., Potential Purine Antagonists. VI. Synthesis of 1–Alkyl–and 1–Aryl–4–substituted Pyrazolo[3,40–d]pyridines, J. Org. Chem. Nov. 1956, 21, 1240–1256.

Nickless et al., A Rapid Chemiluminescent Enzyme–Linked Immunosorbent Assay for Cytomegalovirus Immunoglobulin G Antibodies Using Instant Photographic Film, J. Virological Mehtods 1985, 12, 313–321.

Carter et al., Investigation of a Novel Solid–phase Chemiluminescent Analytical System, Incorporating Photographic Detection, for the Measurement of Glucose, Talanta 1982, 29, 529–531.

Journal of Clinical Immunoassay, vol. 15, No. 4 (1992) 246–51.

J. Biolumin Chemilumin, vol. 10 (1995) 219–27.

Clinical Chemistry, vol. 41, No. 1 (1995) 24–31.

J. Heterocycl. Chem., vol. 30 (1993) 267–73.

J. Org. Chemistry, vol. 21 (1956) 1240–55.

J. Org. Chemistry, vol. 29 (1964) 1915–19.

Tetrahedron Letters, vol. 36 No. 47, Nov. 1995, pp. 8641–8644.

Biochemical and Biophysical Research Communication, vol. 193, No. 2, Jun. 15, 1993, pp. 540–545.

*Primary Examiner*—John Kight
*Assistant Examiner*—Dameron Jones
*Attorney, Agent, or Firm*—Fitzpatrick, Cella, Harper & Scinto

[57] ABSTRACT

Disclosed is a chemiluminescent method of quantitatively determining one of peroxide, a peroxidation-active substance or a pyrazolopyridopyridazine derivative represented by the formula (I):

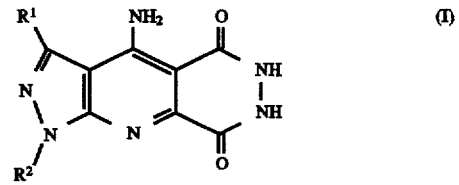

wherein $R^1$ represents hydrogen, lower alkyl, optionally substituted aryl, optionally substituted heterocyclic group, substituted sulfonyl, substituted sulfinyl, substituted thio etc.; $R^2$ represents hydrogen, lower alkyl, optionally substituted aryl, etc., or a salt thereof; characterized by subjecting an unknown amount of one substance selected from the peroxide, peroxidation-active substance and pyrazolopyridopyridazine derivative to react with a known amount of the remaining two substances.

5 Claims, 2 Drawing Sheets

METHOD OF QUANTITATIVE DETERMINATION OF PEROXIDE, A PEROXIDATION-ACTIVE SUBSTANCE OR A PYRAZOLOPYRIDOPYRIDAZINE DERIVATIVE

BACKGROUND OF THE INVENTION

The present invention relates to a chemiluminescent method of quantitative determination of peroxide, a peroxidation-active substance or pyrazolopyridopyridazine derivative.

It is important in analytical chemistry and biochemistry to quantitatively determine with accuracy a peroxide such as hydrogen peroxide, and a peroxidation-active substance such as peroxidase. Various methods of quantitatively determining an intended substance by finally converting it into hydrogen peroxide are frequently employed in the field of clinical inspection. For example, to quantitatively determine glucose in a serum sample, generally employed is a method of applying glucose oxidase to the sample to form hydrogen peroxide followed by measuring the amount of the hydrogen peroxide formed. Further, various oxidases such as cholesterol oxidase, uricase, choline oxidase, etc. are employed to form hydrogen peroxide in the field of clinical inspection.

Methods of quantitative determination of an antigen, antibody or DNA have been known, in which an antigen, antibody or DNA is labeled with oxidase such as peroxidase; and the oxidase activity or the amount of the hydrogen peroxide to be formed by the reaction of the oxidase is quantitatively determined. Conventional calorimetric method to determine the peroxidase activity or the amount of hydrogen peroxide with calorimetric reagent does not always exhibit satisfactory sensitivity.

Recently, attention has been given to the quantitative determination of minor amounts of peroxide, especially lipid peroxide in living organisms and foods. To quantitatively determine these substances, however, conventional colorimetric reagents do not often exhibit satisfactory sensitivity.

Methods of quantitatively determining minor amounts of hydrogen peroxide and peroxidase activity have become much desired.

It is said that among current quantitative determination methods for measuring hydrogen peroxide or peroxidase activity, those using bioluminescence or chemiluminescence have the highest sensitivity. In particular, luminescent compounds such as luminol, isoluminol, lucigenin, acridinium esters, etc. have been well known to be utilizable in chemiluminescence (see Kazuhiro Imai; Bioluminescence and Chemiluminescence, published by Hirokawa Shoten), and systems of clinical diagnosis using such compounds have been known (for example, ACS-180 of Kyowa Medex Co., Ltd., Luminomaster of Sankyo Co., Ltd., Amerlite kits of Amersham Japan, Ltd). Further, the quantitative determination of peroxide or peroxidation-active substance by chemiluminescence using coumarin derivative has been known ( Japanese Published Unexamined Patent Application No. 815219/93).

Compounds having higher luminescent sensitivity are desired.

SUMMARY OF THE INVENTION

The present invention provides a method of quantitatively determining one of peroxide, a peroxidation-active substance or a pyrazolopyridopyridazine derivative in a sample, comprising the steps of:

(a) selecting the pyrazolopyridopyridazine derivative represented by the formula (I):

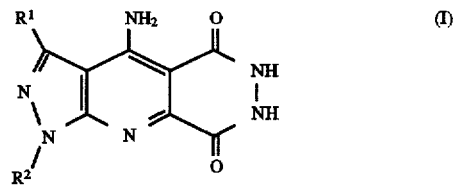

wherein $R^1$ represents hydrogen, lower alkyl, cycloalkyl, lower alkenyl, hydroxyl, lower alkoxy, lower alkanoyl, optionally substituted aryl, optionally substituted heterocyclic group, aralkyl, halogen, cyano, nitro, sulfo, carboxyl, lower alkoxycarbonyl, aryloxycarbonyl, optionally substituted carbamoyl, optionally substituted amino, substituted sulfonyl, substituted sulfinyl or substituted thio; $R^2$ represents hydrogen, lower alkyl, cycloalkyl, lower alkenyl, lower alkanoyl, optionally substituted aryl, optionally substituted heterocyclic group, aralkyl, lower alkoxycarbonyl, aryloxycarbonyl, substituted sulfonyl, substituted sulfinyl or substituted thio, or a salt thereof;

(b) subjecting an unknown amount of one substance selected from the peroxide, peroxidation-active substance and pyrazolopyridopyridazine derivative in the sample to coexist with a known amount of the remaining two substances, to thereby react the unknown amount of the substance with the known amount of the two substances;

(c) measuring the light emission signal generated from the reaction;

(d) determining the substance using a calibration curve previously formed from known amounts of the substance.

The present invention also provides a compound represented by formula (Ia):

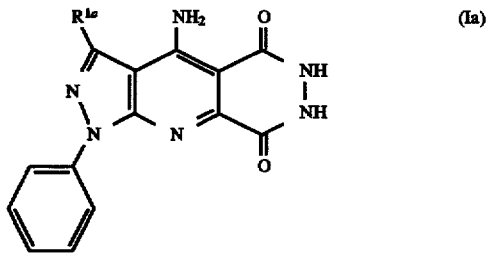

wherein $R^{1a}$ represents lower alkyl, cycloalkyl, lower alkenyl, hydroxyl, lower alkoxy, lower alkanoyl, optionally substituted aryl, optionally substituted heterocyclic group, aralkyl, halogen, cyano, nitro, sulfo, carboxyl, lower alkoxycarbonyl, aryloxycarbonyl, optionally substituted carbamoyl, optionally substituted amino, substituted sulfonyl, substituted sulfinyl or substituted thio. The compounds represented by formulae (I) and (Ia) are hereinafter referred to as Compound (I) and Compound (Ia), respectively.

..●.. shows the results obtained by the use of Compound 2;

-○- shows the result obtained by the use of Compound 3;

-■- shows the result obtained by the use of Compound 4;

-□- shows the result obtained by the use of Compound 5;

-▲- shows the result obtained by the use of Compound 6;

-△- shows the result obtained by the use of luminol.

Figure 2:
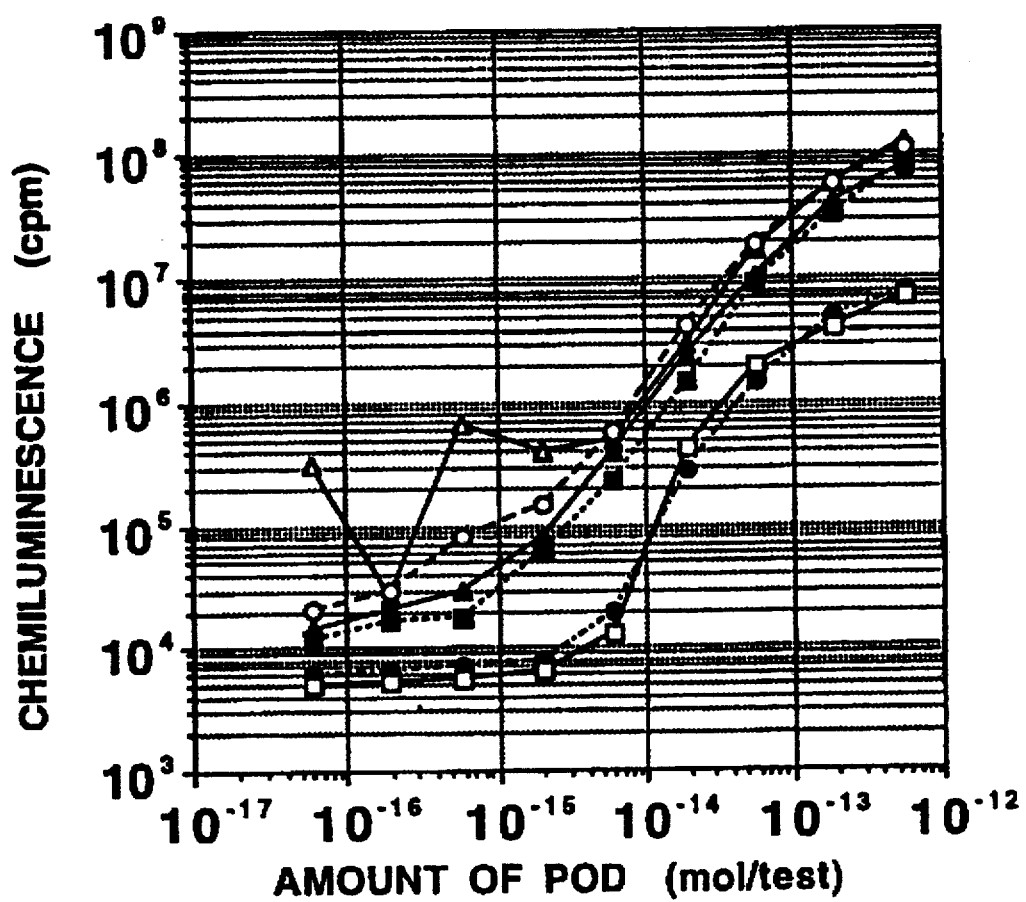

FIG. 2 is a graph showing the results of the quantitative determination of peroxidase by the use of the compound of the present invention and luminol, in terms of the relationship between the amount of the peroxidase (POD) used and the amount of light emission signal for one minute (chemiluminescence, cpm), in which -▲- shows the result obtained by the use of Compound 1;

..○.. shows the result obtained by the use of Compound 5;

..●.. shows the result obtained by the use of Compound 8;

-□- shows the result obtained by the use of Compound 10;

..■.. shows the result obtained by the use of Compound 13;

-△- shows the result obtained by the use of luminol.

DETAILED DESCRIPTION OF THE INVENTION

In the definitions of the groups in formulae (I) and (Ia), the lower alkyl and the alkyl moiety in the lower alkyl, the lower alkoxy, lower alkanoyl and lower alkoxycarbonyl mean linear or branched alkyl having 1 to 6 carbon atoms such as methyl, ethyl, propyl, isopropyl, butyl, isobutyl, sec-butyl, tert-butyl, pentyl, 2-pentyl, 3-pentyl, isoamyl, hexyl, etc. The cycloalkyl means cycloalkyl having 3 to 8 carbon atoms such as cyclopropyl, cyclobutyl, cyclopentyl, cyclohexyl, cycloheptyl, cyclooctyl, etc. The lower alkenyl means linear or branched alkenyl having 2 to 6 carbon atoms such as vinyl, propenyl, butenyl, pentenyl, hexenyl, etc. The aryl and the aryl moiety in the aryloxycarbonyl include, for example, phenyl and naphthyl. The heterocyclic group includes, for example, pyrrolyl, imidazolyl, pyrazolyl, triazolyl, thienyl, furyl, thiazolyl, oxazolyl, oxadiazolyl, pyridyl, pyrazinyl, pyrimidinyl, pyridazinyl, indolyl, benzimidazolyl, indazolyl, benzothiophenyl, benzofuryl, quinolinyl, isoquinolinyl, quinazolinyl, cinnolinyl, quinoxalinyl and phthalazinyl. The aralkyl means aralkyl having 7 to 15 carbon atoms such as benzyl, phenethyl, naphthylmethyl, benzhydryl, etc. The halogen includes, for example, fluorine, chlorine, bromine and iodine atoms.

The substituted aryl and the substituted heterocyclic group each have 1 to 4 independently-selected substituents.

The substituents are, for example, lower alkyl, cycloalkyl, lower alkenyl, hydroxyl, lower alkoxy, lower alkanoyl, aralkyl, halogen, cyano, nitro, sulfo, carboxyl, lower alkoxycarbonyl, optionally substituted carbamoyl and optionally substituted amino. Of these groups, the lower alkyl, the cycloalkyl, the lower alkenyl, the lower alkoxy, the lower alkanoyl, the aralkyl, the lower alkoxycarbonyl and the halogen have the same meanings as described above. The substituted carbamoyl and the substituted amino each have one or two independently-selected substituents. The substituents are, for example, lower alkyl. The lower alkyl has the same meaning as described above.

In formulae (I) and (Ia), the substituted carbamoyl and the substituted amino each have 1 or 2 substituents. The substituents are, for example, optionally substituted lower alkyl, cycloalkyl, lower alkenyl, lower alkanoyl, aryl and aralkyl. Of these groups, the lower alkyl, the cycloalkyl, the lower alkenyl, the lower alkanoyl, the aryl and the aralkyl have the same meanings as described above. The substituted lower alkyl are substituted by, for example, hydroxyl, lower alkoxy, carboxyl, lower alkanoyl and sulfo. The lower alkoxy and the lower alkanoyl have the same meanings as described above.

In formulae (I) and (Ia), the substituted sulfonyl, the substituted sulfinyl and the substituted thio have 1 substituent. The substituent is, for example, optionally substituted lower alkyl, cycloalkyl, lower alkenyl, lower alkanoyl, aryl and aralkyl. Of these groups, the lower alkyl, the cycloalkyl, the lower alkenyl, the lower alkanoyl, the aryl and the aralkyl have the same meanings as described above. The substituted lower alkyl is substituted by, for example, hydroxyl, lower alkoxy, carboxyl, lower alkanoyl and sulfo. The lower alkoxy and the lower alkanoyl have the same meanings as described above.

The peroxidation-active substance for use in the present invention is any substance that exhibits peroxidation activity and includes, for example, peroxidase, iron compounds (e.g., iron chlorides, ion oxides, etc.), iodides (e.g., sodium iodide, ammonium iodide, etc.), molybdates (e.g., phosphomolybdates, etc.), urohemine, hemoglobin, porphyrin compounds, etc. Peroxidase as separated and purified from microorganisms, animals and plants can be used in the present invention and, in addition, commercial products of peroxidase can also be used.

The peroxide for use in the present invention includes, for example, hydrogen peroxide, lipid peroxides, etc.

Compound (I) can be produced in accordance with the methods described in J. Heterocycl. Chem., 30, 267 (1993) or according to the method mentioned below.

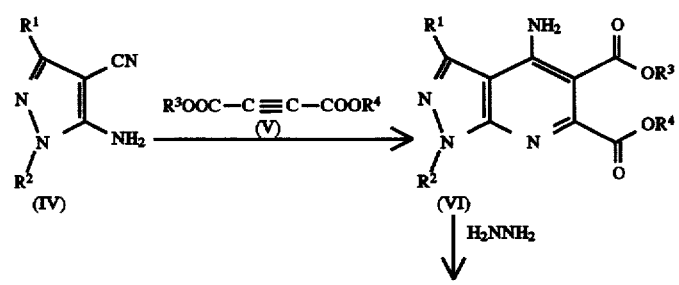

-continued

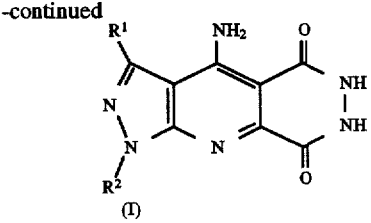

wherein $R^3$ and $R^4$ are the same or different and each represents hydrogen or lower alkyl; $R^1$ and $R^2$ have the same meanings as described above. The alkyl for $R^3$ and $R^4$ has the same meaning as described above.

Compound (VI) is produced by reacting Compound (IV) with Compound (V) in the presence of a base such as potassium carbonate or the like, in a solvent such as dimethylsulfoxide or the like, at a temperature falling between 0° C. and the boiling point of the solvent used, for 0.5 to 100 hours.

The starting Compound (IV) can be obtained in accordance with the methods described in J. Org. Chem., 21, 1240 (1956); J. Org. Chem., 29, 1915 (1964); Chem. Ber., 99, 3492 (1966); etc., or according to the method mentioned below.

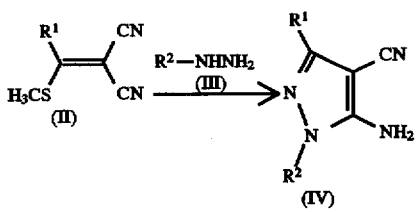

wherein $R^1$ and $R^2$ have the same meanings as described above.

Compound (IV) is produced by reacting Compound (II) with Compound (III) in a solvent, for example, alcohol such as methanol, ethanol or the like, at a temperature falling between room temperature and the boiling point of the solvent used, for 1 minute to 24 hours.

The starting Compound (II) may be commercial product or can be obtained by or in accordance with the method described in Chem. Ber., 99, 2900 (1966), etc.

Of Compound (IV), those where $R^1$ is substituted sulfonyl or substituted sulfinyl (Compound (IVa)) can be obtained by treating Compound (IV) where $R^1$ is substituted thio (Compound (IVb)) with an oxidizing agent such as m-chloro-perbenzoic acid or the like in a solvent such as dichloromethane or the like for 1 minute to 12 hours.

Compound (I) is produced by reacting Compound (VI) with hydrazine in a solvent, for example, alcohol such as methanol, ethanol or the like, at a temperature falling between room temperature and the boiling point of the solvent used, for 1 minute to 12 hours, followed by heating the resulting product at 200° to 350° C. for 1 minute to 12 hours.

The intermediate and the final product as obtained in the above-mentioned methods can be isolated and purified by ordinary isolating and purifying method which is generally employed in the field of organic synthetic chemistry, for example, by filtration, extraction, washing, drying, concentration, recrystallization, various chromatographic means, etc. The intermediate may be directly subjected to the next reaction without being purified.

In the present invention, salt of Compound (I) can be used. As the acceptable salt of Compound (I), acid addition salt and alkaline addition salt are mentioned. Acid addition salts include, for example, inorganic acid addition salt such as hydrochloride, sulfate or phosphate and organic acid addition salts such as acetate, maleate, fumarate or citrate. Alkaline addition salts include, for example, ammonium, lithium, sodium, potassium, calcium and magnesium. Further, Compound (I) may exist as their adducts with water or with various solvents, and such adducts can also be used as the chemiluminescent compound in the present invention.

Specific examples of Compound (I) are listed in Table 1.

TABLE 1

| Compound | $R^1$ | $R^2$ |
|---|---|---|
| 1 | —SOCH₃ | phenyl |
| 2 | H | H |
| 3 | —SCH₃ | H |
| 4 | thienyl | phenyl |
| 5 | —SCH₃ | phenyl |
| 6 | —SO₂CH₃ | phenyl |
| 7 | benzothienyl | phenyl |
| 8 | H | phenyl |
| 9 | —CH₃ | phenyl |

TABLE 1-continued

[Structure: pyridine-based core with R¹–CH=N–N(R²)– substituent, NH₂ group, and two C=O groups forming an NH-NH bridge]

| Compound | R¹ | R² |
|---|---|---|
| 10 | –C₆H₅ (phenyl) | –C₆H₅ (phenyl) |
| 11 | –C₆H₄–N(CH₃)₂ | –C₆H₅ (phenyl) |
| 12 | –S–C₆H₅ | –C₆H₅ (phenyl) |
| 13 | –SO–C₆H₅ | –C₆H₅ (phenyl) |

In the table, Compound 2, Compound 3 and Compound 8 are obtained in accordance with the methods described in J. Heterocycl. Chem.,30, 267 (1993).

Next, the quantitative determination method of the present invention is described hereinunder.

To quantitatively determine peroxide, a known amount of Compound (I) and a peroxidation-active substance are dissolved in buffer having pH of 4 to 12, preferably 6 to 10 to prepare a reaction reagent, and a sample containing peroxide is added thereto and incubated at −10° to 90° C., preferably 20° to 50°C. The light emission signal generated from the reaction is then measured. From the data thus measured, the peroxide in the sample is quantitatively determined with reference to the calibration curve that has been previously obtained from the experimental data of known amounts of the peroxide. The buffer may include aqueous solutions of buffer agents such as phosphate, tris-HCl, acetate, succinate, oxalate, borate, phthalate, glycine and Good reagent. The buffer is used at a concentration of 0.005 to 2 mol/liter, preferably 0.01 to 0.5 mol/liter, more preferably 0.02 to 0.2 mol/liter. Compound (I) maybe adjusted to a concentration of 0.01 μmol/liter to 100 mmol/liter, preferably 0.05 to 20 mmol/liter. The peroxidation-active substance may be adjusted to a concentration of 1×10⁻⁸ to 200 mg/ml, preferably 10 to 100 mg/ml. For example, when peroxidase is used, it is adjusted to a concentration of 1×10⁻⁴ to 100 U/ml, preferably 10 to 50 U/ml.

To quantitatively determine a peroxidation-active substance, Compound (I) and peroxide are dissolved in buffer having pH of 4 to 12, preferably 6 to 10 to prepare a reaction reagent, and a sample containing a peroxidation-active substance is added thereto and incubated at −10° to 90° C., preferably 2°to 50° C. The light emission signal generated from the reaction is then measured. From the data thus measured, the peroxidation-active substance in the sample is quantitatively determined with reference to the calibration curve that has been previously obtained from the experimental data of known amounts of the peroxidation-active substance. As the buffer and the concentration of the buffer, those to be used for the quantitative determination of peroxide can be used. Compound (I) may be adjusted to a concentration of 0.01 μmol/liter to 100 mmol/liter, preferably 0.05 to 20 mmol/liter. The peroxide may be adjusted to a concentration of 0.01 μmol/liter to 100 mmol/liter, preferably 0.05 to 20 mmol/liter.

To quantitatively determine Compound (I), peroxide and a peroxidation-active substance are dissolved in a buffer having pH of 4 to 12, preferably 6 to 10 to prepare a reaction reagent, and a sample containing Compound (I) is added thereto and incubated at −10° to 90° C., preferably 20° to 50° C. The light emission signal generated from the reaction is then measured. From the data thus measured, Compound (I) in the sample is quantitatively determined with reference to the calibration curve that has been previously obtained from the experimental data of known amounts of Compound (I). As the buffer and the concentration of the buffer, those to be used for the quantitative determination of peroxide can be used. The peroxide may be adjusted to a concentration of 0.01 μmol/liter to 100 mmol/liter, preferably 0.05 to 20 mmol/liter. The peroxidation-active substance may be adjusted to a concentration of 1×10⁻⁸ to 200 mg/ml, preferably 10 to 100 mg/ml. For example, when peroxidase is used, it maybe adjusted at a concentration of 1×10⁻⁴ to 100 U/ml, preferably 10 to 50 U/ml.

To quantitatively determine Compound (I), the peroxide or the peroxidation-active substance, a surfactant such as TRITON X-100® (Polyethylene glycol mono-p-isooctylphenyl ether, a registered trademark of Union Chemicals and Plastics Co., Inc.) may be added to the reaction system, if desired. Also if desired, proteins, polyalkyl quaternary amines, fluorescent agents, dimethylsulfoxide, etc. can be used as enhancers. Again, if desired, an alkaline aqueous solution may be added to the reaction system so as to enhance the chemiluminescent reaction. As the proteins, for example, usable are bovine serum albumin (BSA), human serum albumin (HSA), human immunoglobulin, ovalbumin, etc. As the polyalkyl quaternary amines, for example, usable are polydiaryldimethylammonium chlorides, polyalkyldimethylbenzylammonium chlorides, etc. As the fluorescent agents, for example, usable are fluorescein, 4-fluoro-7-nitrobenzofurazan or 7-fluoro-4-nitrobenzoxadiazole as bonded to amines, coumarin compounds, amino acids, peptides or proteins or their derivatives, etc. As the alkaline aqueous solution, for example, usable is an aqueous solution of sodium hydroxide, potassium hydroxide or the like. The amount of the enhancer to be used may be 0.0001 to 10% by weight based on the weight of the reaction system.

The present invention can favorably be applied to any diagnostic detection which is based on the final measurement of peroxide such as hydrogen peroxide, etc. For example, it can be used for the quantitative determination of substrates for specific oxidase (e.g., glucose oxidase, galactoseoxidase, cholesterol oxidase, uricase, etc.) based on their specificity and also for the measurement of the activity of enzymes such as monoamine oxidase, choline esterase, etc.

In addition, the present invention can also be favorably applied to enzyme-immunoassay, in which the substances to be measured may include chemicals and hormones to be in serum, urine, etc., minor components to be derived from various disorders, etc.

For the immunoassay to which the present invention is applied, employable are enzyme-immunoassay and various methods described in Studies on Medicine (1987). As one example of the methods, an antigen is reacted with a fixed antibody and the antigen is reacted with an enzyme-labeled antibody to measure the amount of the antigen.

Again, the present invention is applicable to methods of measuring polynucleotides, which are described in, for example, DNA Probes (published by Jisk Co., 1988), DNA Probes II (published by Jisk Co., 1990), etc.

The amount of light emission signal generated from the reaction is measured by determining the integrated quantity of light for a determined period of time or throughout the reaction.

To quantitatively determine the light emission signal according to the present invention, employable are known methods, for example, a method of applying the signal onto a light-sensitive photographic film to thereby record the intensity of the light emission on the film, a method of measuring the intensity of the light emission by the use of a measuring device equipped with a photomultiplier (see Kazuhiro Imai; Bioluminescence and Chemiluminescence, published by Hirokawa Shoten), a method of using a photocounter, etc.

Next, embodiments of the present invention are described in detail by means of the following examples, which, however, are not intended to restrict the scope of the present invention.

EXAMPLE 1

Synthesis of 4-amino-3-methylsulfinyl-1-phenyl-1H-pyrazolo[4',3':5, 6]pyrido[2,3-d]pyridazine-5,8 (6H,7H)dione (Compound 1)

(1) Synthesis of 5-amino-3-methylthio-1-phenylpyrazole-4-carbonitrile

A mixture comprised of 17.0 g (100 mmol) of bis(methylthio)methylenepropanedinitrile, 10.8 g (100mmol) of phenylhydrazine and 80 ml of ethanol was heated under reflux for 2 hours. The solvent was removed through distillation, and 20 ml of ethanol was added to the residue, which was thus crystallized. The resulting crystals were taken out by means of filtration under suction to give 20.9 g (9.1 mmol) of the entitled product as colorless, needle-like crystals having a melting point of from 136° to 137° C. The yield was 91%.

(2) Synthesis of dimethyl 4-amino-3-methylthio-1-phenyl-1H-pyrazolo[3,4-b]pyridine-5,6-dicarboxylate A dimethylsulfoxide (20 ml) solution of 9.0 g (63 mmol) of dimethyl acetylenedicarboxylate was dropwise added to a mixture comprised of 11.5 g (50 mmol) of 5-amino-3-methylthio-1-phenylpyrazole-4-carbonitrile, 20.8 g (145 mmol) of anhydrous potassium carbonate and 300 ml of dimethylsulfoxide, while stirring and cooling with ice, and then stirred for further 60 hours at room temperature. During the stirring, the reaction liquid was changed from brown to greenish brown. After the reaction, the liquid reaction mixture was poured into 500 ml of water with ice and stirred for 30 minutes at room temperature. The blackish brown solid thus precipitated was taken out, and 20 ml of methanol was added thereto and heated. The white crystals thus formed were taken out by means of filtration under suction and recrystallized from methanol to obtain 4.80 g (12.8 mmol) of the entitled product as colorless, needle-like crystals having a melting point of 120° to 122° C.

(3) Synthesis of dimethyl 4-amino-3-methylsulfinyl-1-phenyl-1H-pyrazolo[2,3-b]pyridine-5,6-dicarboxylate A dichloromethane (20 ml) solution of 2.34 g (10 mmol) of 70% m-chloro-perbenzoic acid was added to a dichloromethane (50 ml) solution of 3.74 g (10 mmol) of dimethyl 4-amino-3-methylthio-1-phenyl-1H-pyrazolo[3,4-b]pyridine-5,6-dicarboxylate over a period of 20 minutes, and then the mixture was vigorously stirred for 30 minutes. The solvent was removed through distillation, and the residue was washed with methanol to obtain 3.26 g (8.40 mmol) of the entitled product as a colorless solid. The yield was 84%. The product was further recrystallized from methanol to give colorless, needle-like crystals having a melting point of 146° to 148° C.

(4) Synthesis of 4-amino-3-methylsulfinyl-1-phenyl-1H-pyrazolo[4',3':5,6]pyrido[2,3-d]pyridazine-5,8(6H,7H)dione (Compound 1)

0.388 g (1.0 mmol) of dimethyl 4-amino-3-methylsulfinyl-1-phenyl-1H-pyrazolo[2,3-b]pyridine-5,6dicarboxylate and 5 ml of hydrazine hydrate were added to 50 ml of methanol and heated under reflux for 2 hours. After the reaction, methanol and the excess hydrazine hydrate were removed through distillation. 20 ml of methanol was added to the residue to wash the residue, and methanol was filtered under suction to obtain a solid. The thus-obtained product was heated at 250° to 300° C. on a hot plate for 30 minutes, and then well washed with methanol to give 0.312 g (0.88 mmol) of the entitled product as a powdery compound. The yield was 88%. The product was recrystallized from a mixture of dimethylsulfoxide and methanol to give the desired product as colorless crystals having a melting point of 360° C. or higher.

IR (KBr) vcm$^{-1}$: 3420, 3320, 3170, 3100–2800 (broad), 1650 (CO), 1590, 1565, 1500.

UV (ethanol) λmax nm: 246, 299, 346; λmin nm: 220, 280, 320.

NMR (DMSO-d$_6$) δ: 3.09 (3H, s, SOCH$_3$), 7.31–7.68 (3H, m, C$_6$H$_5$—H), 8.23–8.40 (2H, m, C$_6$H$_5$—H), 8.81 (1H, brs, NH or OH), 10.07 (1H, brs, NH or OH), 10.65 (1H, brs, NH or OH), 11.58 (1H, brs, NH or OH).

LR-MS m/z (%): 357 (M$^+$+1, 22), 356 (M$^+$, 100), 341 (72), 340 (65), 307 (19), 293 (15).

EXAMPLE 2

Synthesis of 4-amino-1-phenyl-3-(thiophen-2-yl)-1H-pyrazolo[4',3':5,6]pyrido[2,3-d]pyridazine-5,8 (6H,7H)dione (Compound 4)

(1) Synthesis of 5-amino-1-phenyl-3-(thiophen-2-yl)pyrazole-4-carbonitrile

Using 2.06 g (10 mmol) of methylthio(thiophen-2-yl)methylenepropanedinitrile and 1.1 g (10 mmol) of phenylhydrazine, the entitled product having a melting point of 165° to 167° C. was obtained in the same manner as in Example 1-(1).

(2) Synthesis of dimethyl 4-amino-1-phenyl-3-(thiophen-2-yl)pyrazolo[3,4-b]pyridine-5,6-dicarboxylate A dimethylsulfoxide (20 ml) solution of 10.0 g (70 mmol) of dimethyl acetylenedicarboxylate was dropwise added to a mixture comprised of 2.66 g (10 mmol) of 5-amino-1-phenyl-3-(thiophen-2-yl)pyrazole-4-carbonitrile, 27.6 g (200 mmol) of anhydrous potassium carbonate and 300 ml of dimethylsulfoxide, while cooling with ice, over a period of 30 minutes, and then stirred for further 60 hours at room temperature. During the stirring, the reaction liquid was changed from brown to greenish brown. After the reaction, the liquid reaction mixture was poured into 500 ml of water with ice and stirred for 30 minutes at room temperature. The blackish brown solid thus precipitated was taken out by filtration, dried in air and added to 20 ml of methanol. The white crystals thus formed were taken out by filtration and recrystallized from methanol to obtain 3.50 g of the entitled product as colorless crystals having a melting point of 178° to 180° C.

(3) Synthesis of 4-amino-1-phenyl-3-(thiophen-2-yl)-1H-pyrazolo[4',3':5,6]pyrido[2,3-d]pyridazine-5,8(6H,7H)dione (Compound 4)

0.34 g (1.0 mmol) of dimethyl 4-amino-1-phenyl-3-(thiophen-2-yl)pyrazolo[3,4-b]pyridine-5,6-dicarboxylate and 5 ml of hydrazine hydrate were added to 50 ml of methanol and heated under reflux for 2 hours. After the reaction, methanol and the excess hydrazine hydrate were removed by distillation. 20 ml of methanol was added to the residue to wash the residue, and methanol was filtered under suction to obtain a solid. The thus-obtained product was heated at 250° to 300° C. on a hot plate for 30 minutes, and then well washed with methanol to give 0.342 g (0.91 mmol) of the entitled product as a powder. The yield was 91%. The product was recrystallized from a mixture of dimethylsulfoxide and methanol to give colorless, needle-like crystals having a melting point of 355° to 366° C.

IR (KBr) vcm$^{-1}$: 3450, 3250, 3170 (NH or OH), 3000 (broad), 1650 (CO), 1595, 1490, 1370.

UV (ethanol) λmax nm: 240, 309, 343, 350; λmin nm: 215, 310, 330.

NMR (DMSO-$d_6$) δ: 7.25–7.68 (5H, m, $C_4H_3S$—H and $C_6H_5$—H), 7.79 (1H, dd, J=1.2, 5.0 Hz, 5'-H), 8.30–8.41 (2H, m, $C_6H_5$—H).

LR-MS m/z (%): 377 (M$^+$+1, 25) 376 (M$^+$, 100), 291 (14), 77 (6).

EXAMPLE 3

Synthesis of 4-amino-3-methylthio-1-phenyl-1H-pyrazolo[4',3':5,6]pyrido[2,3-d]pyridazine-5,8(6H,7H)dione (Compound 5)

0.37 g (1.0 mmol) of dimethyl 4-amino-3-methylthio-1-phenyl-1H-pyrazolo[3,4-b]pyridine-5,6-dicarboxylate and 5 ml of hydrazine hydrate were added to 50 ml of methanol and heated under reflux for 2 hours. After the reaction, methanol and the excess hydrazine hydrate were removed by distillation. 20 ml of methanol was added to the residue to wash the residue, and methanol was filtered under suction to obtain yellow, needle-like crystals. The thus-obtained product was heated at 250° to 300° C. on a hot plate for 30 minutes, whereupon the compound was decolored from yellow to almost colorless. The compound was then well washed with methanol to obtain 0.313 g (0.92 mmol) of the entitled compound as a powdery product having a melting point of 355° to 358° C. (with decomposition). The yield was 92%.

IR (KBr) vcm$^{-1}$: 3500, 3425, 3260, 3160, 3050 (broad), 2950, 1650 (CO), 1595, 1575, 1500, 1370.

UV (ethanol) λmax nm: 235, 255, 297, 304; λmin nm: 208, 225, 250.

NMR (DMSO-$d_6$) δ: 2.76 (3H, s, SCH3), 7.22–7.64 (3H, m, $C_6H_5$—H), 8.26–8.40 (2H, m, $C_6H_5$—H), 9.81 (2H, brs, NH or OH), 11.55 (2H, brs, NH or OH)

LR-MS m/z (%): 341 (M$^+$+1, 21), 340 (M$^+$, 100), 325 (4), 308 (6), 307 (30), 293 (7), 77 (18), 44 (8).

EXAMPLE 4

Synthesis of 4-amino-3-methanesulfonyl-1-phenyl-1H-pyrazolo[4',3':5,6]pyrido[2,3-d]pyridazine-5,8(6H,7H)dione (Compound 6)

(1) Synthesis of dimethyl 4-amino-3-methanesulfonyl-1-phenyl-1H-pyrazolo[3,4-b]pyridine-5,6-dicarboxylate A dichloromethane (40 ml) solution of 5.82 g (24 mmol) of 70% m-chloro-perbenzoic acid was added to a dichloromethane (50 ml) solution of 3.74 g (10 mmol) of dimethyl 4-amino-3-methylthio-1-phenyl-1H-pyrazolo[3,4-b]pyridine-5,6-dicarboxylate as obtained in Example 1-(2), over a period of 20 minutes, and then the mixture was vigorously stirred for 1 hour. The solvent was removed by distillation, and the residue was washed with methanol to obtain 3.18 g (7.87 mmol) of the entitled product as a colorless solid. The yield was 79%. The product was further recrystallized from methanol to give colorless, needle-like crystals having a melting point of from 187° to 189° C.

(2) Synthesis of 4-amino-3-methanesulfonyl-1-phenyl-1H-pyrazolo[4',3':5,6]pyrido[2,3-d]pyridazine-5,8(6H,7H)dione (Compound 6)

0.404 g (1.0 mmol) of dimethyl 4-amino-3-methanesulfonyl-1-phenyl-1H-pyrazolo[3,4-b]pyridine-5,6-dicarboxylate and 5 ml of hydrazine hydrate were added to 50 ml of methanol and heated under reflux for 2 hours. After the reaction, methanol and the excess hydrazine hydrate were removed by distillation. 20 ml of methanol was added to the residue to wash the residue, and methanol was filtered under suction to obtain yellow, needle-like crystals. The thus-obtained product was heated at 250° to 300°C. on a hot plate for 30 minutes, and then well washed with methanol to give 0.355 g (0.90 mmol) of the entitled product as a powdery compound. The yield was 90%. Next, the product was recrystallized from a mixture of dimethylsulfoxide and methanol to give colorless crystals having a melting point of 360° C. or higher.

IR (KBr) vcm$^{-1}$: 3380, 3200, 3000, 2920, 1650 (CO), 1366, 1310, 1130, 560.

UV (ethanol) λmax nm: 246, 300, 345; λmin nm: 220, 275, 290.

NMR (DMSO-$d_6$) δ: 3.61 (3H, s, SO$_2$CH$_3$), 7.45–7.72 (3H, m, $C_6H_5$—H), 8.15 (1H, brs, NH or OH, 8.23–8.34 (2H, m, $C_6H_5$—H), 10.31 (1H, brs, NH or OH), 11.18 (1H, brs, NH or OH).

LR-MS m/z (%) : 373 (M$^+$+1, 22), 372 (M$^+$, 100), 199 (13), 78 (43), 77 (23), 69 (12), 63 (43).

EXAMPLE 5

Synthesis of 4-amino-3-(benzothiophen-2-yl)-1-phenyl-1H-pyrazolo[4',3':5,6]pyrido[2,3d]-pyridazine-5,8(6H,7H)dione (Compound 7)

(1) Synthesis of 5-amino-3-(benzothiophen-2-yl)-1-phenylpyrazole-4-carbonitrile

Using 2.56 g (10 mmol) of (benzothiophen-2-yl)(methylthio)methylenepropanedinitrile and 1.1 g (10 mmol) of phenylhydrazine, the entitled product having a melting point of 260° to 262° C. was obtained in the same manner as in Example 1-(1).

(2) Synthesis of dimethyl 4-amino-3-(benzothiophen-2-yl)pyrazolo[3,4-b]pyridine-5,6-dicarboxylate Using 3.16 g (10 mmol) of 5-amino-3-(benzothiophen-2-yl)-1-phenylpyrazole-4-carbonitrile and 1.42 g (10 mmol) of dimethyl acetylenedicarboxylate, the entitled product having a melting point of 218° to 220° C. was obtained in the same manner as in Example 2-(2).

(3) Synthesis of 4-amino-3-(benzothiophen-2-yl)-1-phenyl-1H-pyrazolo[4',3':5,6]pyrido[2,3-d]pyridazine-5,8(6H,7H)dione (Compound 7)

0.458 g (1.0 mmol) of dimethyl 4-amino-3-(benzothiophen-2-yl)-1-phenylpyrazolo[3,4-b]pyridine-5,6-dicarboxylate and 5 ml of hydrazine hydrate were added to 50 ml of methanol and heated under reflux for 2 hours. After the reaction, methanol and the excess hydrazine hydrate were removed by distillation. 20 ml of methanol was added to the residue to wash the residue, and methanol was filtered under suction to obtain yellow, needle-like crystals. The thus-obtained product was heated at 250° to 300° C. on a hot plate for 30 minutes, and then well washed with methanol to give 0.405 g (0.95 mmol) of the entitled product as a powder. The yield was 95%. Next, the product was recrystallized from a mixture of dimethylsulfoxide and methanol to give a colorless, powdery compound having a melting point 350° to 361° C.

IR (KBr) vcm$^{-1}$: 3430, 3170, 3000 (broad), 1650 (CO), 1600, 1490, 1365, 805.

UV (ethanol) λmax nm: 231, 317; λmin nm: 215, 305.

NMR (DMSO-d$_6$) δ: 7.28–7.68 (5H, m, aromatic ring-H), 7.92–8.11 (2H, m, aromatic ring-H), 7.92 (1H, s, 3'-H), 8.23–8.43 (2H, m, aromatic ring-H), 9.97 (1H, brs, NH or OH), 11.02 (2H, brs, NH or OH).

LR-MS m/z (%): 426 (M$^+$, 8), 278 (8), 256 (5), 45 (100).

EXAMPLE 6

Synthesis of 4-amino-3-methyl-1-phenyl-1H-pyrazolo[4',3':5,6]pyrido[2,3-d]pyridazine-5,8(6H,7H)dione (Compound 9 )

(1) Synthesis of dimethyl 4-amino-3-methyl-2-phenylpyrazolo[3,4-b]pyridine-5,6-dicarboxylate Using 3.96 g (20 mmol) of 5-amino-3-methylpyrazole-4-carbonitrile [see J. Org. Chem., 21, 1240 (1956)] and 2.84 g (20 mmol) of dimethyl acetylenedicarboxylate, the entitled product having a melting point of 190° to 191° C. was obtained in the same manner as in Example 2-(2).

(2) Synthesis of 4-amino-3-methyl-1-phenyl-1H-pyrazolo[4',3':5,6]pyrido[2,3-d]pyridazine-5,8(6H,7H)dione (Compound 9)

0.34 g (1.0 mmol) of dimethyl 4-amino-3-methyl-1-phenylpyrazolo[3,4-b]pyridine-5,6-dicarboxylate and 5 ml of hydrazine hydrate were added to 50 ml of methanol and heated under reflux for 2 hours. After the reaction, methanol and the excess hydrazine hydrate were removed through distillation. 20 ml of methanol was added to the residue to wash the residue, and methanol was filtered under suction to obtain yellow, needle-like crystals. The thus-obtained product was heated at from 250° to 300° C. on a hot plate for 30 minutes, and then well washed with methanol to give 0.262 g 0.85 mmol) of the entitled product as a powder. The yield was 85%. Next, the product was recrystallized from a mixture of dimethylsulfoxide and methanol to give pale-yellow, needle-like crystals having a melting point of 340° to 342° C.

IR (KBr) vcm$^{-1}$: 3480, 3400, 3280, 3000 (broad), 1640 (CO), 1595, 1500.

UV (ethanol) λmax nm: 254, 345; min nm: 220, 300.

NMR (DMSO-d$_6$) δ: 2.74 (3H, s, CH$_3$), 7.18–7.72 (3H, m, C$_6$H$_5$—H), 8.26–8.40 (2H, m, C$_6$H$_5$—H), 9.90 (1H, brs, NH or OH), 10.82 (2H, brs, NH or OH).

LR-MS m/z (%) : 309 (M$^+$+1, 17), 308 (M$^+$, 86), 256 (5), 23 (8), 45 (100).

EXAMPLE 7

Synthesis of 4-amino-1,3-diphenyl-1H-pyrazolo[4',3':5,6]pyrido[2,3-d]pyridazine-5,8(6H,7H)dione (Compound 10)

(1) Synthesis of dimethyl 4-amino-1,3-diphenylpyrazolo[3,4-b]pyridine-5,6-dicarboxylate Using 2.60 g (10 mmol) of 5-amino-1,3-diphenylpyrazole-4-carbonitrile [see J. Org. Chem., 29, 1915 (1964)] and 1.42 g (10 mmol) of dimethyl acetylenedicarboxylate, the entitled product having a melting point of 277° to 279° C. was obtained in the same manner as in Example 2-(2).

(2) Synthesis of 4-amino-1,3-diphenyl-1H-pyrazolo[4',3':5,6]pyrido[2,3-d]pyridazine-5,8(6H,7H)dione (Compound 10)

0.402 g (1.0 mmol) of dimethyl 4-amino-1,3-diphenylpyrazolo[3,4-b]pyridine-5,6-dicarboxylate and 5 ml of hydrazine hydrate were added to 50 ml of methanol and heated under reflux for 2 hours. After the reaction, methanol and the excess hydrazine hydrate were removed through distillation. 20 ml of methanol was added to the residue to wash the residue, and methanol was filtered under suction to obtain yellow, needle-like crystals. The thus-obtained product was heated at 250° to 300° C. on a hot plate for 30 minutes, and then well washed with methanol to give 0.315 g (0.85 mmol) of the entitled product as a powder. The yield was 85%. Next, the product was recrystallized from a mixture of dimethylsulfoxide and methanol to give a colorless powdery compound having a melting point of 358° to 368° C.

IR (KBr) vcm$^{-1}$: 3470, 3405, 3180, 3000 (broad), 1650 (CO), 1495, 1490.

UV (ethanol) λmax nm: 235, 255, 346; λmin nm: 215, 240, 300.

NMR (DMSO-d$_6$) δ: 6.50 (1H, brs, NH), 7.25–7.85 (8H, m, C$_6$H$_5$—H), 8.32–8.45 (2H, m, C$_6$H$_5$—H), 10.64 (1H, brs, NH or OH), 11.25 (1H, brs, NH or OH).

LR-MS m/z (%): 371 (M$^+$+1, 22), 370 (M$^+$, 100), 285 (10), 83 (11), 45 (49), 44 (25).

EXAMPLE 8

Synthesis of 4-amino-3-(p-dimethylaminophenyl)-1-phenyl-1H-pyrazolo[4',3':5,6]pyrido[2,3-d]pyridazine-5,8(6H,7H)dione (Compound 11)

(1) Synthesis of dimethyl 4-amino-3-(p-dimethylaminophenyl)-1-phenylpyrazolo[3,4-b]pyridine-5,6-dicarboxylate Using 1.57 mg (5 mmol) of 5-amino-3-(p-dimethylaminophenyl)-1-phenylpyrazole-4-carbonitrile [see Chem. Ber., 99, 3492 (1966)] and 0.85 g (6 mmol) of dimethyl acetylenedicarboxylate, the entitled product having a melting point of 207° to 208° C. was obtained in the same manner as in Example 2-(2).

(2) Synthesis of 4-amino-3-(p-dimethylaminophenyl)-1-phenyl-1H-pyrazolo[4',3':5,6]pyrido[2,3-d]pyridazine-5,8 (6H,7H)dione (Compound 11)

0.445 g (1.0 mmol) of dimethyl 4-amino-3-(p-dimethylaminophenyl)-1-phenylpyrazolo[3,4-b]pyridine-5, 6-dicarboxylate and 5 ml of hydrazine hydrate were added to 50 ml of methanol and heated under reflux for 2 hours. After the reaction, methanol and the excess hydrazine hydrate were removed by distillation. 20 ml of methanol was added to the residue to wash the residue, and methanol was filtered under suction to obtain yellow, needle-like crystals. The thus-obtained product was heated at 250° to 300° C. on a hot plate for 30 minutes, and then well washed with methanol to obtain 0.382 g (0.92 mmol) of the entitled product as a powder. The yield was 92%. Next, the product was recrystallized from a mixture of dimethylsulfoxide and methanol to give a colorless powdery compound having a melting point of from 315° to 321° C.

IR (KBr) vcm$^{-1}$: 3455, 3170, 3000 (broad), 1650 (CO), 1610, 1595, 1490, 1350.

UV (ethanol) λmax nm: 249, 268, 326; λmin nm: 220, 250, 310.

NMR (DMSO-d$_6$) δ: 3.30 [6H, s, N(CH$_3$)$_2$], 6.51 (1H, brs, NH or OH), 6.93 (2H, d, J=8.7 Hz, C$_6$H$_5$—H), 7.33 (1H, m, C$_6$H$_5$—H), 7.53–7.62 (5H, m, C$_6$H$_5$—H, NH or OH), 8.41 (2H, d, J=8.7 Hz, C$_6$H$_5$—H), 9.90 (1H, s, NH or OH), 11.61 (1H, s, NH or OH).

LR-MS m/z (%): 414 (M$^+$+1, 28), 413 (M$^+$, 100), 398 (3), 328 (3), 207 (6), 164 (4), 44 (2).

EXAMPLE 9

Synthesis of 4-amino-1-phenyl-3-phenylthio-1H-pyrazolo[4',3':5,6]pyrido[2,3-d]pyridazine-5,8(6H,7H)dione (Compound 12)

(1) Synthesis of 5-amino-1-phenyl-3-phenylthiopyrazole-4-carbonitrile

A mixture comprised of 14.7 g (50 mmol) of bis(phenylthio)methylenepropanedinitrile [see Chem. Ber., 99, 2900 (1966)], 6.5 g (60 mmol) of phenylhydrazine and 80 ml of methanol was heated under reflux for 7 hours. The solvent was removed by distillation, and 100 ml of ethanol was added to the residue to crystallize the residue. The crystals formed were taken out by filtration under suction to obtain 13.7 g (47mmols) of the intended product as colorless, needle-like crystals having a melting point of 172° to 173° C. The yield was 94%.

(2) Synthesis of dimethyl 4-amino-1-phenyl-3-phenylthiopyrazolo[3,4-b]pyridine-5,6-dicarboxylate Using 3.1 g (11 mmol) of 5-amino-1-phenyl-3-phenylthiopyrazole-4-carbonitrile, 2.0 g (14 mmol) of dimethyl acetylenedicarboxylate and 6.0 g (43 mmol) of anhydrous potassium carbonate, the intended product having a melting point of 160° to 161° C. was obtained in the same manner as in Example 2-(2).

(3) Synthesis of 4-amino-1-phenyl-3-phenylthio-1H-pyrazolo[4',3':5,6]pyrido[2,3-d]pyridazine-5,8(6H,7H)dione (Compound 12)

0.88 g (2.0 mmol) of dimethyl 4-amino-1-phenyl-3-phenylthiopyrazolo[3,4-b]pyridine-5,6-dicarboxylate and 5 ml of hydrazine hydrate were added to 50 ml of methanol and heated under reflux for 2 hours. After the reaction, methanol and the excess hydrazine hydrate were removed by distillation. 20 ml of methanol was added to the residue to wash the residue, and methanol was filtered under suction to obtain yellow, needle-like crystals. The thus-obtained product was heated at 250° to 300° C. on a hot plate for 30 minutes, and then well washed with methanol to give 0.70 g (1.72 mmol) of the entitled product as colorless, needle-like crystals. The yield was 86%.

IR (KBr) vcm$^{-1}$: 3430, 3260 (NH or OH), 3180 (NH or OH), 3050–2600 (broad, NH or OH), 1650 (CO), 1593, 1572, 1489, 1358.

UV (ethanol) λmax nm: 201, 246, 299, 348, 360; λmin nm: 220, 288, 328.

NMR (CDCl$_3$) δ: 7.23–7.42 (6H, m, C$_6$H$_5$—H), 7.50–7.56 (2H, m, C$_6$H$_5$—H), 7.90–8.12 (2H, m, NH), 8.34–8.38 (2H, m, C$_6$H$_5$—H), 9.91 (1H, brs, NH or OH), 11.58 (1H, brs, NH or OH).

LR-MS m/z (%): 403 (M$^+$+1, 27), 402 (M$^+$, 100), 401 (12), 293 (13), 58 (14), 56 (13), 45 (22), 44 (17).

EXAMPLE 10

Synthesis of 4-amino-1-phenyl-3-phenylsulfinyl-1H-pyrazolo[4',3':5,6]pyrido[2,3-d]pyridazine-5,8(6H,7H)dione (compound 13)

(1) Synthesis of dimethyl 4-amino-1-phenyl-3-phenylsulfinyl-1H-pyrazolo[2,3-b]pyridine-5,6-dicarboxylate Using 0.87 g (2 mmol) of dimethyl 4-amino-1-phenyl-3-phenylthiopyrazolo[3,4-b]pyridine-5,6-dicarboxylate as obtained in Example 9-(2) and 0.49 g (2 mmol) of m-chloroperbenzoic acid, the entitled product having a melting point of from 214° to 215° C. was obtained in the same manner as in Example 4-(1).

(2) Synthesis of 4-amino-1-phenyl-3-phenylsulfinyl-1H-pyrazolo[4',3':5,6]pyrido[2,3-d]pyridazine-5,8(6H,7H)dione (Compound 13)

0.45 g (1.0 mmol) of dimethyl 4-amino-1-phenyl-3-phenylsulfinyl-1H-pyrazolo[2,3-b]pyridine-5,6-dicarboxylate and 5 ml of hydrazine hydrate were added to 50 ml of methanol and heated under reflux for 2 hours. After the reaction, methanol and the excess hydrazine hydrate were removed by distillation. 20 ml of methanol was added to the residue to wash the residue, and this was filtered under suction to obtain yellow, needle-like crystals. The thus-obtained product was heated at 250° to 300° C. on a hot plate for 30 minutes, and then well washed with methanol to give 0.32 g (0.766 mmol) of the entitled product as a powder. The yield was 76%. Next, the product was recrystallized from a mixture of dimethylsulfoxide and methanol to give colorless crystals having a melting point of from 314° to 316° C.

IR (KBr) vcm$^{-1}$: 1648 (CO), 1490, 1375.

UV (ethanol) λmax nm: 203, 242, 300, 347; λmin nm: 220, 282, 318.

NMR (DMSO-d$_6$) δ: 7.58–7.62 (6H, m, C$_6$H$_5$—H), 7.79 (2H, m, C$_6$H$_5$—H), 8.31 (2H, m, C$_6$H$_5$—H), 8.77 (½H, brs, NH or OH), 10.10 (½H, s, NH or OH), 11.70 (½H, s, NH or OH).

LR-MS m/z (%): 419 (M$^+$+1, 26), 418 (M$^+$, 100), 402 (12), 370 (24), 309 (18), 293 (16), 77 (12).

EXAMPLE 11

100 U of peroxidase, 50 mg of TRITON X-100® and 10 mg of a compound to be tested or luminol (control compound) were dissolved in 100 ml of 20 mm phosphate buffer (pH 8.0) to prepare a liquid reagent.

400 µl of the liquid reagent was put into a test tube and left at 37° C. for 10 minutes, and the test tube was set on a photometer (Lumicounter 1000 Model, produced by Niti-on I-Rika-Kikai Seisaku-sho Co.) which was kept at a constant temperature of 37° C. 10 µl of 90 µmol/liter hydrogen peroxide and 10 µl of aqueous, 1N sodium hydroxide solution were added thereto, and the light emission signal was measured by determining the integrated quantity of light for one minute (cpm). The data obtained are shown in Table 2.

TABLE 2

| Compound | light Emission signal (cpm) | Compound | light Emission signal (cpm) |
|---|---|---|---|
| Luminol | 4.5 × 10$^5$ | 7 | 1.8 × 10$^6$ |
| 1 | 3.9 × 10$^7$ | 8 | 2.4 × 10$^6$ |
| 2 | 1.9 × 10$^6$ | 9 | 4.7 × 10$^6$ |
| 3 | 1.5 × 10$^7$ | 10 | 8.9 × 10$^5$ |
| 4 | 1.7 × 10$^6$ | 11 | 5.2 × 10$^5$ |
| 5 | 2.8 × 10$^7$ | 12 | 7.4 × 10$^6$ |
| 6 | 4.6 × 10$^7$ | 13 | 2.8 × 10$^7$ |

As is obvious from Table 2, the light emission signal from the compound of the present invention is higher than that from luminol.

EXAMPLE 12

100 U of peroxidase, 50 mg of TRITON X-100® and 10 mg of Compound 1, Compound 2, Compound 3, Compound 4, Compound 5, Compound 6 or luminol (control compound) were dissolved in 100 ml of 20 mM phosphate buffer (pH 8.0) to prepare a liquid reagent.

400 µl of the liquid reagent was put into a test tube and left at 37° C. for 10 minutes, and the test tube was set on a photometer (Lumicounter 1000 Model, produced by Niti-on I-Rika-Kikai Seisaku-sho Co.) which was kept at a constant temperature of 37° C. 10 µl of hydrogen peroxide with a varying concentration and 10 μl of aqueous, sodium hydroxide solution (1N) were added thereto, and the light emission signal (chemiluminescent) was measured by determining the integrated quantity of light for one minute (cpm).

Figure 1:
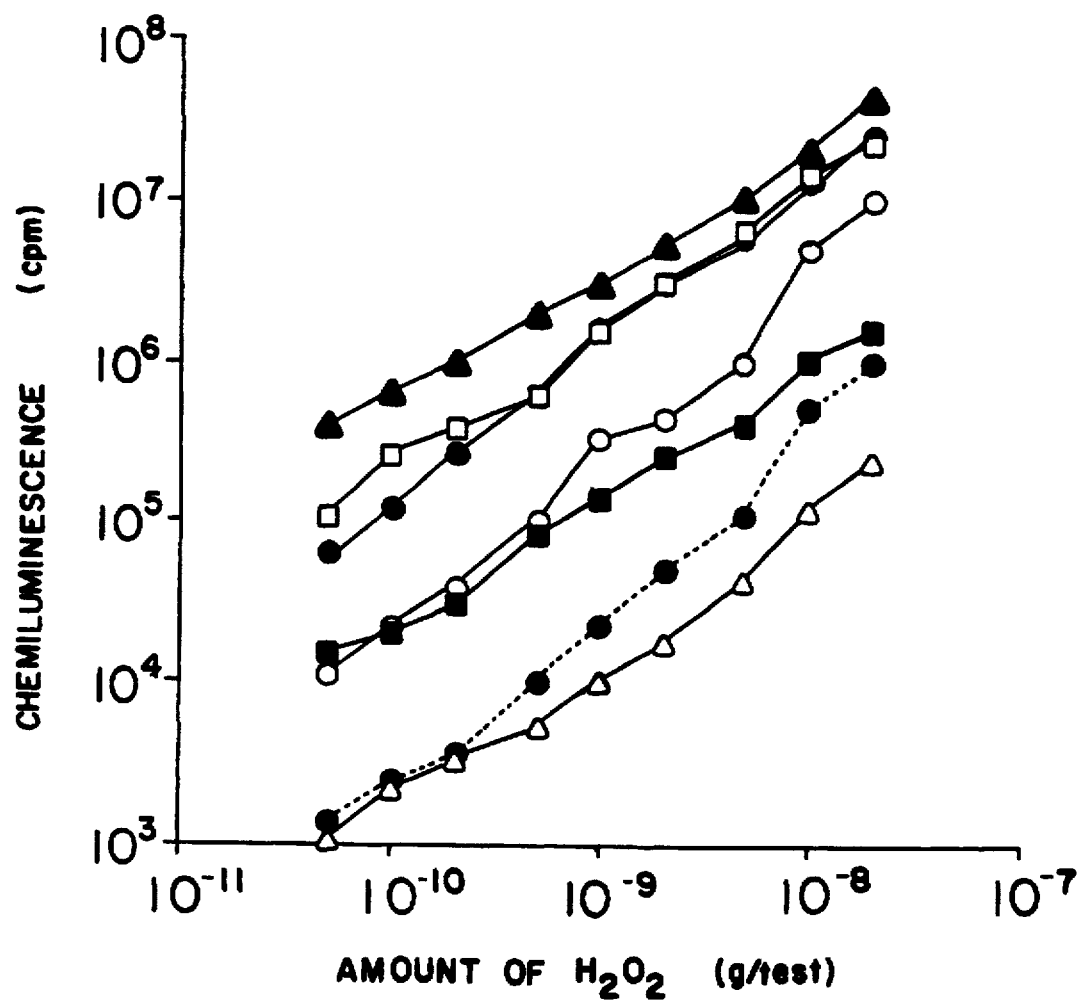
FIG. 1 is a graph showing the results of the quantitative determination of hydrogen peroxide by the use of the compounds of the present invention and luminol, in terms of the relationship between the amount of hydrogen peroxide used and the amount of light emission signal for one minute (chemiluminescence, cpm), in which -●- shows the result obtained by the use of Compound 1.

The data obtained are shown in FIG. 1.

As is obvious from FIG. 1, the emission sensitivity to hydrogen peroxide of the compounds of the present invention is higher than that of luminol.

EXAMPLE 13

50 mg of TRITON X-100® and 10 mg of Compound 1, Compound 5, Compound 8, Compound 10, Compound 13 or luminol (control compound) were dissolved in 100 ml of 20 mM phosphate buffer (pH 8.0) to prepare a liquid reagent.

400 μl of the liquid reagent was put into a test tube and left at 37° C. for 10 minutes, and the test tube was set on a photometer (Lumicounter 1000 Model, produced by Niti-on I-Rika-Kikai Seisaku-sho Co.) which was kept at a constant temperature of 37° C. 10 μl of 300 mmol/liter hydrogen peroxide and 10 μl of a peroxidase solution with a varying concentration were added thereto, and the light emission signal (chemiluminescent) was measured by determining the integrated quantity of light for one minute (cpm).

The data obtained are shown in FIG. 2.

As is obvious from FIG. 2, the light emission signal from the compound of the present invention is higher than that from luminol.

As has been described hereinabove, it is possible to quantitatively determine one of peroxide, a peroxidation-active substance or Compound (I) at high sensitivity according to the present invention While the invention has been described in detail and with reference to specific embodiments thereof, it will be apparent to one skilled in the art that various changes and modifications can be made therein without departing from the spirit and scope thereof.

What is claimed is:

1. A method of quantitatively determining the amount substance selected from a of one of peroxide, a peroxidation-active substance or a pyrazolopyridopyridazine derivative in a sample, comprising the steps of:

(a) selecting the pyrazolopyridopyridazine derivative represented by the formula (I):

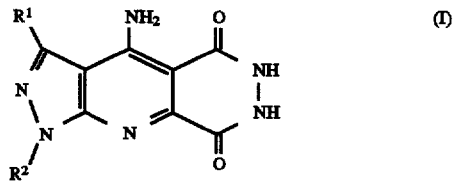

wherein $R^1$ represents hydrogen, lower alkyl, cycloalkyl, lower alkenyl, hydroxyl, lower alkoxy, lower alkanoyl, optionally substituted aryl, optionally substituted heterocyclic group, aralkyl, halogen, cyano, nitro, sulfo, carboxyl, lower alkoxycarbonyl, aryloxycarbonyl, optionally substituted carbamoyl, optionally substituted amino, substituted sulfonyl, substituted sulfinyl or substituted thio; $R^2$ represents hydrogen, lower alkyl, cycloalkyl, lower alkenyl, lower alkanoyl, optionally substituted aryl, optionally substituted heterocyclic group, aralkyl, lower alkoxycarbonyl, aryloxycarbonyl, substituted sulfonyl, substituted sulfinyl or substituted thio, or a salt thereof;

(b) subjecting an unknown amount of one substance selected from the peroxide, peroxidation-active substance and pyrazolopyridopyridazine derivative in the sample to coexist with a known amount of the remaining two substances, to thereby react the unknown amount of the substance with the known amount of the two substances; the known amount of the peroxide being in the range of 0.01 μmol/liter to 100 mmol/liter, peroxidation-active substance being in the range of $1\times10^{-8}$ mg/ml to 200 mg/ml, and pyrazolopyridopyridazine derivative being in the range of 0.01 μmol/liter to 100 mmol/liter;

(c) measuring the light emission signal generated from the reaction;

(d) determining the substance using a calibration curve previously formed from known amounts of the substance.

2. The method according to claim 1, wherein the peroxide is hydrogen peroxide.

3. The method according to claim 1, wherein the peroxidation-active substance is peroxidase.

4. The method according to claim 1, wherein the light emission signal is measured by light-sensitive photographic film, a photomultiplier or a photocounter.

5. A Compound represented by the formula (Ia):

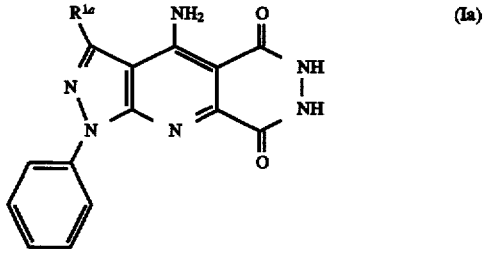

wherein $R^{1a}$ represents lower alkyl, cycloalkyl, lower alkenyl, hydroxyl, lower alkanoyl, optionally substituted heterocyclic group selected from the group consisting of imidazolyl, pyrazolyl, triazolyl, thienyl, furyl, thiazolyl, oxazolyl, oxadiazolyl, pyridyl, pyrazinyl, pyrimidinyl, pyridazinyl, indolyl, benzimidazolyl, indazolyl, benzothiophenyl, benzofuryl, quinolinyl, isoquinolinyl, quinazolinyl, cinnolinyl, quionoxalinyl and phthalizinyl, aralkyl, nitro, sulfo, carboxyl, lower alkoxycarbonyl, aryloxycarbonyl, optionally substituted carbamoyl, optionally substituted amino, substituted sulfonyl, substituted sulfinyl or substituted thio.

* * * * *

UNITED STATES PATENT AND TRADEMARK OFFICE
CERTIFICATE OF CORRECTION

PATENT NO. : 5,801,008

DATED : September 1, 1998

INVENTOR(S) : YOSHINORI TOMINAGA, ET AL.

It is certified that error appears in the above-identified patent and that said Letters Patent is hereby corrected as shown below:

ON THE TITLE PAGE AT [56]
OTHER PUBLICATIONS, In "Cheng et al.,", "Pyrazolo[3,40-d]py-" should read --Pyrazolo[3,4-d]py- --;
OTHER PUBLICATIONS, In "Nickless et al.,", "Mehtods" should read --Methods--.

COLUMN 1
Line 49, "end" should read --and--.

COLUMN 7
Line 61, "2°to" should read --20° to--.

COLUMN 8
Line 10, "50" should read --50°--;
Line 22, "maybe" should read --may be--;
Line 28, "Chemicals" should read --Carbide Chemicals--;
Line 53, "galactoseoxidase" should read --galactose oxidase--.

COLUMN 10
Line 11, "6dicarboxylate" should read --6-dicarboxylate--.

COLUMN 11
Line 51, "$C_{6H5}$-H)," should read --$C_6H_5$-H),--.

UNITED STATES PATENT AND TRADEMARK OFFICE
CERTIFICATE OF CORRECTION

PATENT NO. : 5,801,008

DATED : September 1, 1998

INVENTOR(S) : YOSHINORI TOMINAGA, ET AL.

It is certified that error appears in the above-identified patent and that said Letters Patent is hereby corrected as shown below:

COLUMN 13
Line 39, "0.85 mmol)" should read --(0.85mmol)--;
Line 46, "min" should read --λmin--.

COLUMN 16
Line 28, "20mm" should read --20mM--.

COLUMN 17
Line 39, "amount" should read --amount of--;
Line 40, "of one" should read --one--.

COLUMN 18
Line 21, "reaction;" should read --reaction; and--;
Line 32, "Compound" should read --compound--;
Line 51, "quionoxalinyl" should read --quinoxalinyl-- and "phthalizinyl," should read --phthalazinyl,--.

Signed and Sealed this

First Day of June, 1999

Q. TODD DICKINSON

Attest:

*Attesting Officer*      *Acting Commissioner of Patents and Trademarks*